United States Patent [19]
Vaitekunas

[11] Patent Number: 5,449,370
[45] Date of Patent: Sep. 12, 1995

[54] BLUNT TIPPED ULTRASONIC TROCAR

[75] Inventor: Jeffrey J. Vaitekunas, West Chester, Ohio

[73] Assignee: Ethicon, Inc., Somerville, N.J.

[21] Appl. No.: 60,897

[22] Filed: May 12, 1993

[51] Int. Cl.⁶ .................. A61B 17/32; A61B 17/70
[52] U.S. Cl. ................................. 606/169; 604/22
[58] Field of Search ............ 606/127, 128, 169, 185; 604/22; 128/24 AA

[56] References Cited

U.S. PATENT DOCUMENTS

| | | | |
|---|---|---|---|
| 4,870,953 | 10/1989 | Don Michael et al. | 604/22 |
| 4,897,079 | 1/1990 | Zaleski et al. | 604/22 |
| 4,931,047 | 6/1990 | Broadwin et al. | 606/169 |
| 4,979,952 | 12/1990 | Kubota et al. | 128/24 AA |
| 5,011,471 | 4/1991 | Miyazaki et al. | 604/22 |
| 5,026,387 | 6/1991 | Thomas | 604/22 |
| 5,112,300 | 5/1992 | Ureche | 604/22 |
| 5,123,903 | 6/1992 | Quaid et al. | 606/169 |
| 5,160,317 | 11/1992 | Costin | 604/22 |
| 5,180,363 | 1/1993 | Idemoto et al. | 604/22 |
| 5,190,517 | 3/1993 | Zieve et al. | 604/22 |

FOREIGN PATENT DOCUMENTS

| | | | |
|---|---|---|---|
| 1098003 | 3/1981 | Canada | 604/22 |
| 61-265136 | 5/1985 | Japan . | |
| 1388002 | 4/1988 | U.S.S.R. | 604/22 |
| WO92/14514 | 9/1992 | WIPO . | |

Primary Examiner—Stephen C. Pellegrino
Assistant Examiner—Nancy Mulcare
Attorney, Agent, or Firm—Susan M. Schmitt

[57] ABSTRACT

A blunt tipped trocar which uses ultrasonic energy in the form of vibrations to assist a user in penetrating tissue. In one embodiment of the invention, a feedback mechanism is provided which senses a variation in load on the trocar tip and adjusts the ultrasonic energy level of the vibrating tip in accordance with the load condition. Another embodiment of the invention provides a trocar with a self-contained ultrasonic generator.

33 Claims, 15 Drawing Sheets

BLUNT TIPPED ULTRASONIC TROCAR

FIELD OF THE INVENTION

This invention relates to trocars used to puncture tissue for accessing areas of the body to perform endoscopic surgery and, in particular, to a blunt tipped trocar which uses ultrasonic energy to assist in puncturing tissue.

BACKGROUND OF THE INVENTION

A trocar assembly for use in endoscopic surgical procedures generally comprises two major components, a trocar obturator and a tube or cannula. Typically, the obturator is initially positioned within the cannula and has a sharp and pointed puncturing tip which is extendable from the cannula. The obturator tip is used to penetrate the skin and underlying tissue to provide cannula access to a body cavity. The obturator is then removed and endoscopic surgery performed through the cannula.

Many trocars have safety shields which can cover the tip of the obturator. If the trocar is disarmed, the safety shield is maintained in its tip covering position. When the trocar assembly is engaged for puncturing, the safety shield can be moved to expose the puncturing tip. A user then applies a force to the trocar and the obturator is used to puncture skin and tissue to reach the location for surgery. When the force is released, the safety shield re-covers the obturator tip.

It requires a mechanical force to puncture the skin and muscles to reach soft tissue, typically the desired location for surgery. In abdominal surgery, for example, the abdominal wall which comprises epidermal layers, fascia, muscle and peritoneum is punctured to reach internal viscera. Frequently when the soft tissue is reached, there is a sudden release in resistance to the puncturing force, at which point the user releases the force to avoid undesired puncturing of other tissue with the sharp obturator point as the safety shield covers the obturator tip.

It is therefore an object of this invention to provide a trocar which further reduces any risk of injury to soft or underlying tissue, from a puncturing obturator tip. It is also an object of the invention to provide a trocar which assists the user in puncturing tissue, thereby reducing the necessary amount of user force and enabling greater and easier user control. It is another object of the invention to provide a trocar which would not require a safety shield.

SUMMARY OF THE INVENTION

The present invention provides a blunt tipped trocar for use in endoscopic surgery, for example, to puncture the abdominal wall for access to organs or other tissue for the performance of surgery. More particularly the present invention provides a blunt tipped trocar which uses ultrasonic energy delivered to its tip to assist the insertion of a trocar obturator and cannula. The blunt or rounded obturator tip configuration of the present invention reduces the risk of unintended injury while the ultrasonic energy enables the trocar assembly to penetrate tissue with relatively less force than known trocar assemblies.

In a preferred embodiment of the invention, a shut off mechanism is provided which turns off the device when the trocar has penetrated a patient's outer tissue, e.g., a patient's abdominal wall. A feedback mechanism is used to determine when the tip of the device has penetrated tissue at which point the ultrasonic energy delivered to the tip is shut off or lowered to an inactive idling state.

In one embodiment, the feedback mechanism comprises a tissue acoustical impedance feedback system in which a light sensor located on an inactive portion of the trocar assembly, preferably on the obturator housing, is used to detect light emitted from a light source and reflected from an active portion of the ultrasonic obturator to determine the load or impeding effect of tissue on the trocar tip.

In another embodiment the feedback mechanism comprises a passive piezo electric element located within a piezoelectric stack of an ultrasonic transducer. The passive element vibrates with the other piezoelectric ceramic elements of the stack but unlike the other elements, is not energized. The vibration of the passive element creates an oscillating voltage across the element which corresponds to the vibrations of the piezoelectric stack. From the voltage across the element the load on the trocar can be determined by methods well-known in the art. The passive element may be coupled to a control means of a generator used to supply electrical energy to the ultrasonic transducer to cause vibrations.

Other feedback systems may also be used, for example, a pressure detector or strain gauge may be used to detect tissue absence or presence or tissue type. Electrical parameters may be used to sense and determine the variation in load conditions on the obturator tip as acoustical impedance is related to the system impedance of the generator and trocar assembly. In such a system, either phase differences of voltage and current or magnitude ratios of voltage and current supplied to the handpiece, are used to make this determination. As the load is increased, the phase difference between the voltage and current changes from a resonant state of 0° to a negative phase angle difference related to the load condition.

The feedback system may also be adapted to sense tissue characteristics, such as hard or soft tissue. Different tissue types have different acoustical impedances which effect the tip loading characteristics. The feedback may also be used by the control means to adjust the ultrasonic energy level of the vibrating tip in accordance with the load condition, e.g., by increasing the energy out put by the generator when load increases. Thus a relatively stable energy level may be provided at the obturator tip.

Another feature of the preferred embodiment provides a reset mechanism which must be used every time the trocar is turned off by the shut off mechanism before it can be powered up again.

Another embodiment of the present invention provides for ultrasonic transducer elements which are integral with the obturator shaft.

Another embodiment of the invention provides a self-contained ultrasonic generator wherein the electronic elements are contained within the trocar handle.

DETAILED DESCRIPTION OF THE DRAWINGS

DETAILED DESCRIPTION OF THE PREFERRED EMBODIMENT

Figure 1:
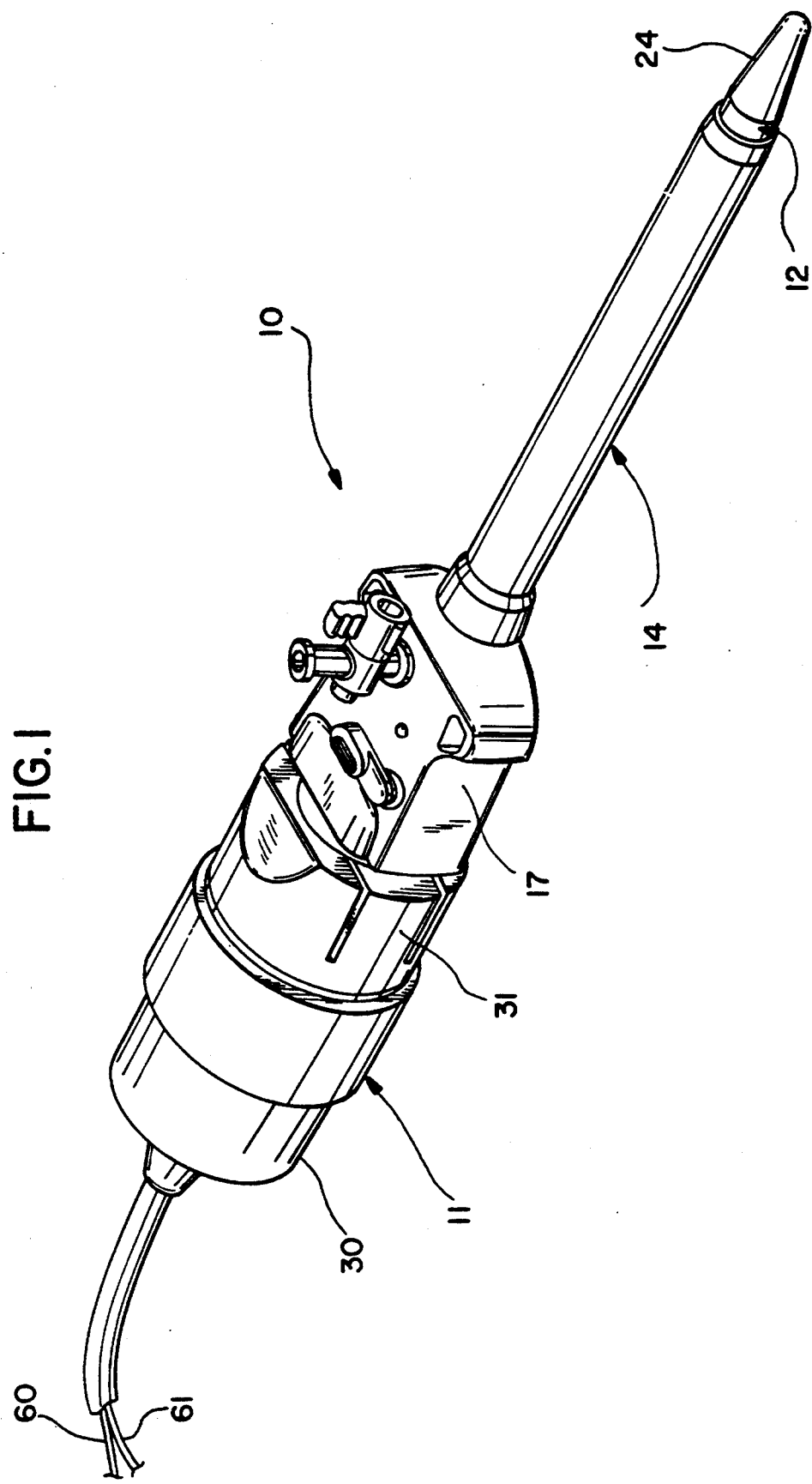
FIG. 1 illustrates a trocar assembly of one embodiment of the present invention.

Referring now to FIGS. 1-8 there is illustrated a trocar assembly 10 comprising a housing 11, a trocar obturator 12 and a cannula assembly 14.

The obturator 12 is the active portion of the trocar assembly, that is, it transmits ultrasonic energy or vibrates at an ultrasonic frequency. The obturator 12 comprises an end mass 20, a transducer 21, an amplifier 22, a waveguide shaft 23 and a blunt puncturing tip 24.

The end mass 20 is engageably coupled at its distal end to the proximal end of the transducer 21. The transducer 21 is comprised of transducer elements. In the preferred embodiment illustrated in FIG. 2, the transducer is a PZT stack comprised of alternating active electrodes 25 and ground electrodes 26, with piezoelectric ceramic transducer elements 27 alternating between electrodes 25 and 26. Each of the active electrodes 25, ground electrodes 26 and ceramic elements 27 has a bore through its center. The active electrodes are electrically connected to a wire 60 and the ground electrodes 26 are electrically connected to a ground wire 61. The wires 60 and 61 lead to a generator 62 external to the trocar assembly 10. In an alternative embodiment the transducer elements may be magnetorestrictive.

One of the ground electrodes is a mounting diaphragm 28 which is in contact with the inside of the housing 11 as described below. A bolt 29 is used to couple the end mass 20 to the transducer 21, and the transducer 21 to the amplifier 22. The bolt 29 is inserted from the proximal end of the end mass 20 through a bore in the end mass 20 and the bores in the electrodes 25, 26 and ceramic elements 27 of the transducer located distally of the end mass 20. The bolt 29, threaded on its distal end, is screwed into a threaded bore on the proximal end of the amplifier 22. The proximal end of the obturator amplifier 22 has an o-ring 42 which is situated in a groove 43, in the amplifier 22. The distal end of the amplifier 22 is coupled to the proximal end of the waveguide 23. The distal end of the waveguide 23 is coupled to the proximal end of the tip 24. The tip 24 is tapered toward the distal end of obturator 12 where tip 24 presents a rounded profile.

Figure 2:
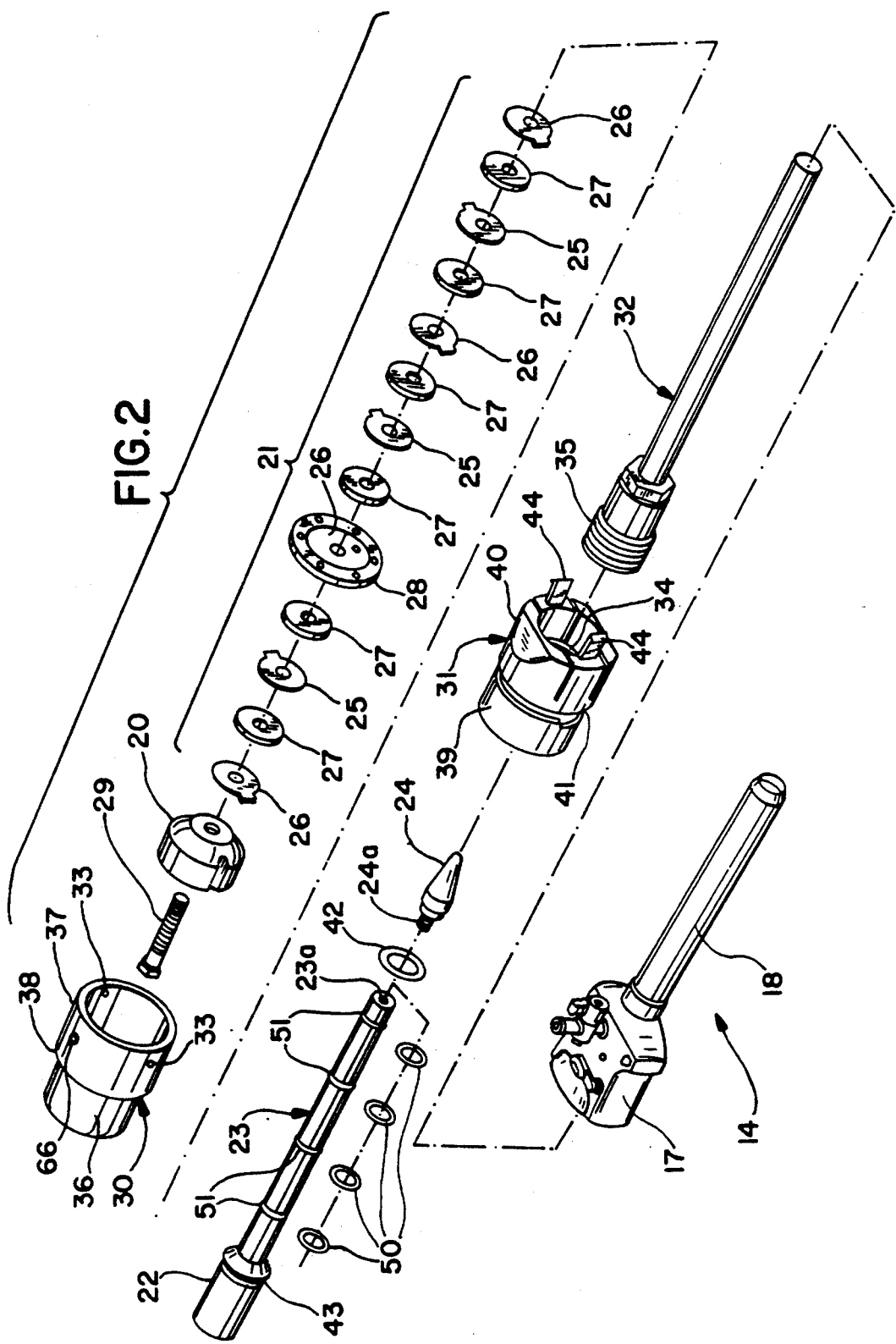
FIG. 2 illustrates an exploded perspective view of a trocar assembly of FIG. 1.
Figure 3:
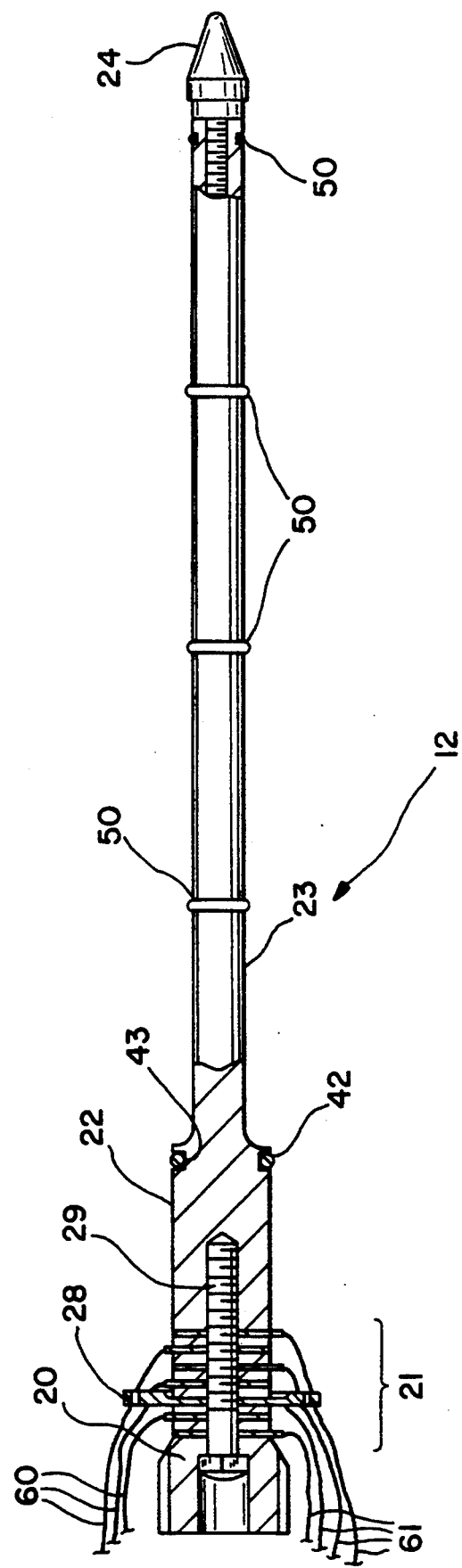
FIG. 3 illustrates a cross-sectional plan view of the trocar obturator of FIGS. 1 and 2.
Figure 4:
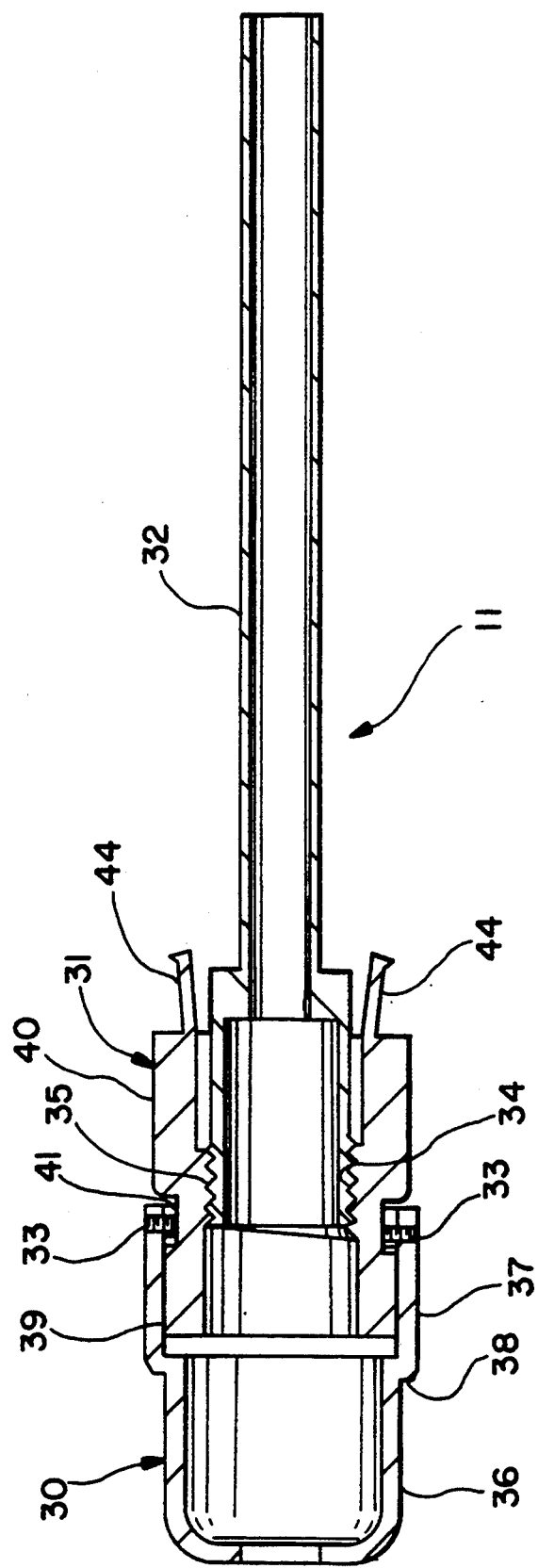
FIG. 4 illustrates a cross-sectional plan view of the housing of FIGS. 1 and 2.
Figure 5:
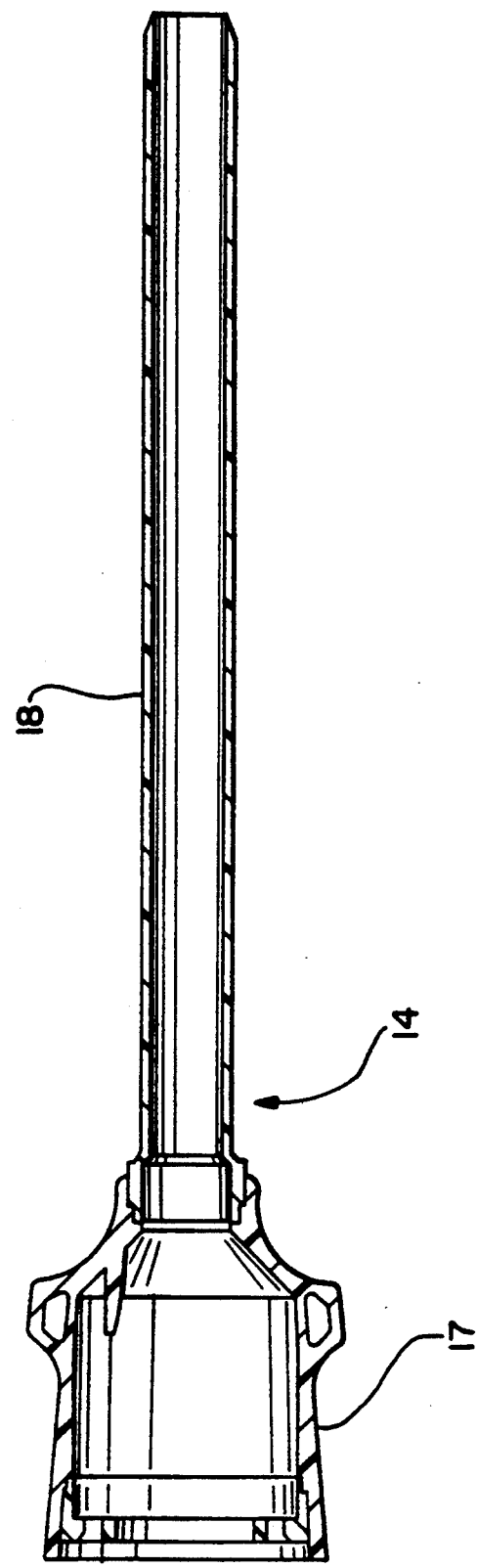
FIG. 5 illustrates a cross-sectional plan view of the cannula assembly of FIGS. 1 and 2.

The tip may be integral with the waveguide or may be attached, for example, as illustrated in FIG. 2 by screwing a threaded proximal end 24a into a threaded bore 23a in the waveguide. In the embodiment in FIGS. 1-8, the waveguide comprises a series of o-rings 50 distributed along its length. The o-rings 50 comprise a non-conductive plastic spaced at equal distances along the shaft at nodal points, i.e., points at a distance along the shaft equal to an integer multiple of $\frac{1}{2}$ wavelength of a predetermined ultrasonic frequency. In other words the nodal points are points located along the length of the waveguide where the sine wave of the ultrasonic vibration amplitude, i.e., the vibrational energy, is equal to zero. The waveguide 23 and tip 24 are preferably made from a solid core shaft constructed of a material which efficiently propagates ultrasonic energy, such as an alloy of aluminum or titanium.

The housing 11 comprises an end cap 30, a connector 31 and a sheath 32. The sheath 32 is preferably comprised of a material which has low thermal and electrical conductivity, and a low coefficient of friction, such as teflon or polycarbonate. The end cap 30 is located on the distal end of the housing 11 and acts as a handle for the user to hold and manipulate the trocar assembly 10. The end cap 30 has an upper circumferential portion 36 and a lower circumferential portion 37. The lower circumferential portion 37 has a larger diameter than the upper circumferential portion 36, and thus forms a lip 38 where it meets the upper circumferential portion 36. The connector 31 has an upper circumferential portion 39 and a lower circumferential portion 40. The lower circumferential portion 40 has a larger diameter than the upper circumferential portion 39 and thus forms a lip 41 where it meets the upper circumferential portion 39.

The proximal end of the obturator 12 including the end mass 20 and transducer 21 are inserted into the end cap 30 so that the diaphragm 28, which has a larger diameter than the electrodes 25, electrodes 26 and ceramic elements 27, rests on the lip 38. The upper portion 39 of the connector means 31 is inserted into and connected to the inner circumference of the lower portion 37 of the end cap 30 by bolts 33. The obturator mounting diaphragm 28 is then engaged between the lip 38 and the proximal end of the upper portion 39 by a pressing force, thus coupling the obturator 12 to the housing 11. The lip 41 of the connector means 31 rests against the distal end of the end cap 30.

The connector 31 has a threaded bore 34 on its distal end. The housing sheath 32 has a threaded proximal end 35 which is screwed into the threaded bore 34.

The housing sheath 32 fits over the obturator amplifier 22 and waveguide 23 with the distal end of the tip 24 extending from the distal end of the sheath 32. The o-rings 50 serve as a means to isolate the vibrating portions of the waveguide 23 from the inner wall of the housing sheath 32 in order to avoid dampening of the ultrasonic wave transmission. Thus the housing 11 is in contact with the obturator only in two places: at the diaphragm 28 and at the o-ring 42, both of which are located at nodal points. The housing avoids contact between the user holding the handpiece and the active portion, i.e., the obturator.

Figure 8:
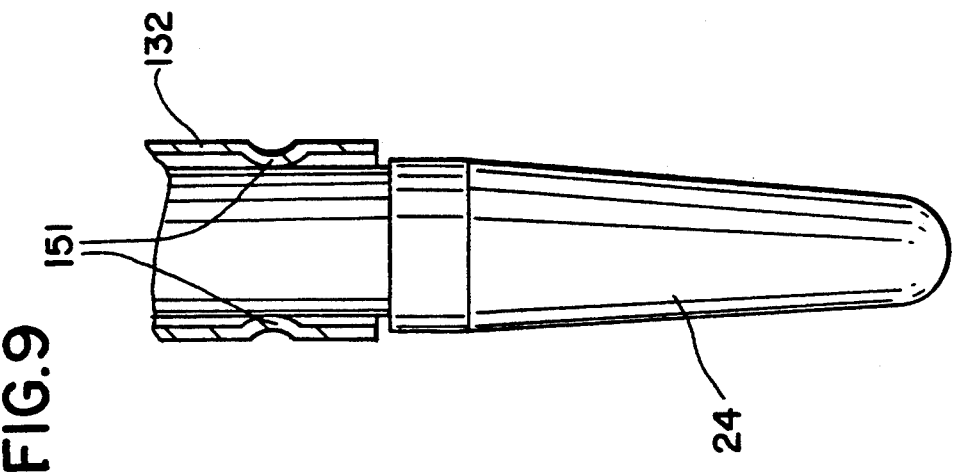
FIG. 8 illustrates a distal portion of the trocar assembly illustrated in FIGS. 1 and 2.

FIG. 8 illustrates an enlarged view of the trocar tip 24 and waveguide 23. A means for isolating the waveguide from the housing sheath is illustrated wherein the means comprises notches 51 in the waveguide 23 to accommodate the o-rings 50. The notch 51 enables the o-ring 50 to lie close to the waveguide circumference and thereby enable a snug fit with the housing sheath 32.

Figure 9:
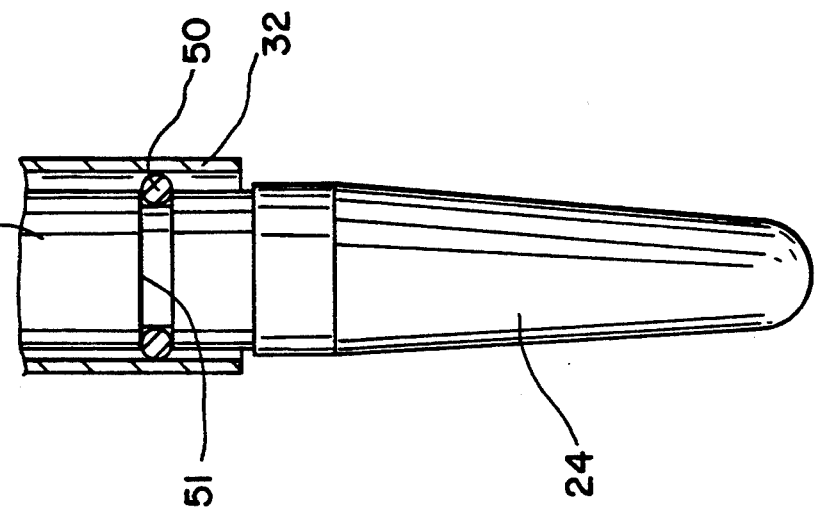
FIG. 9 illustrates a distal portion of trocar assembly of another embodiment of the present invention.

FIG. 9 illustrates another embodiment of an isolation means. The housing 11 comprises a sheath 132 with protrusions 151 extending inward from the inner circumference of the housing sheath to contact the shaft. The protrusions 151 are located at nodal points so that minimal vibrations are transferred to the sheath and minimal dampening of the ultrasonic energy occurs. A further embodiment of the isolation means may comprise rings which are molded into the obturator shaft.

The cannula assembly 14 comprises a handle portion 17 and a cannula tube 18. The housing sheath 32 and waveguide 23 fit within the cannula tube 18. The tip 24 extends out of the distal end of the cannula tube 18. The cannula tube 18 is tapered at its distal end.

The housing 11 is coupled to the cannula handle portion 17 by way of a coupling means 44, at the distal end of the housing connector 31, adapted to be received by the proximal end of the cannula handle 17.

Figure 7:
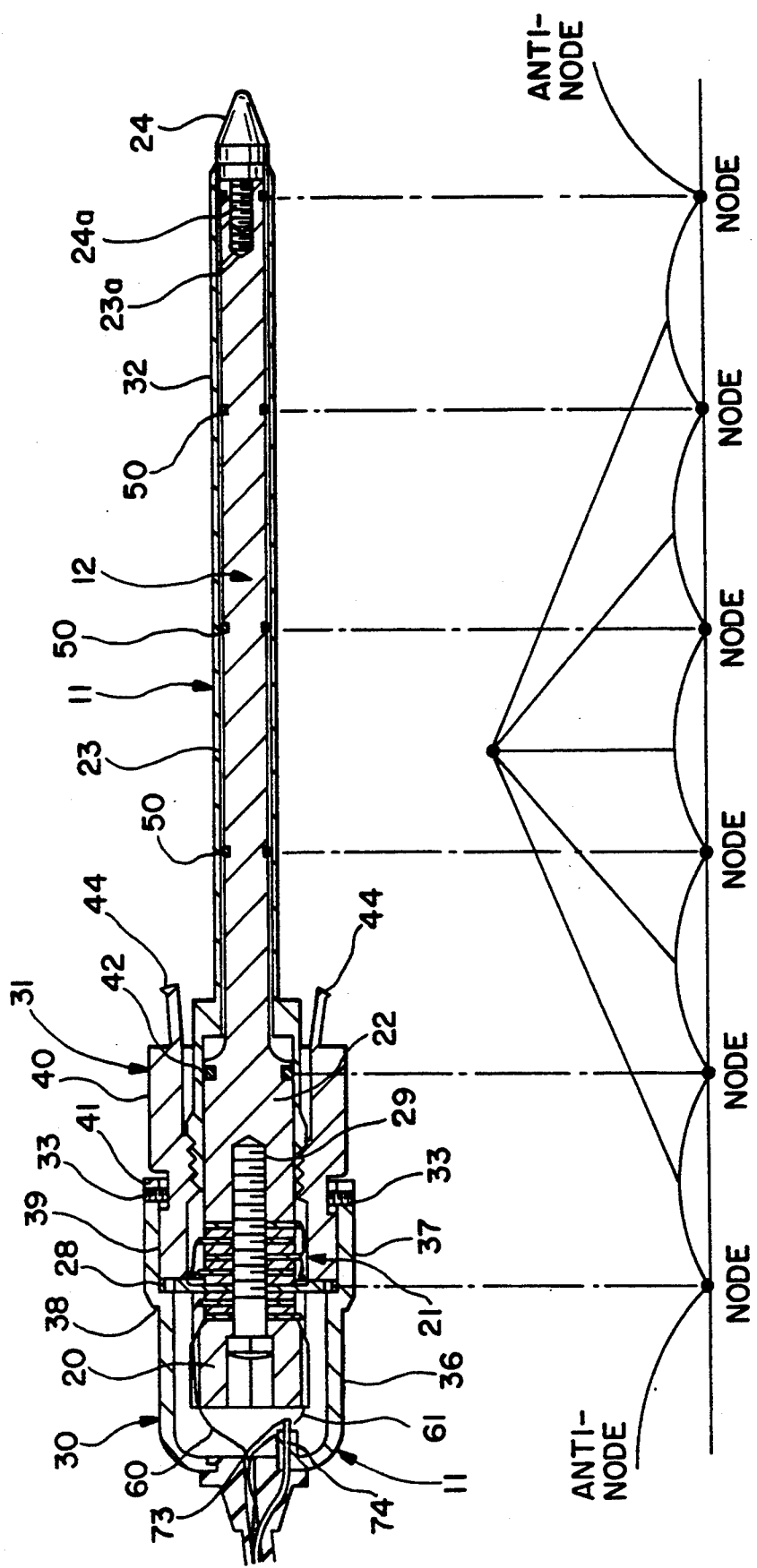
FIG. 7 illustrates a cross sectional plan view of the trocar assembly of FIGS. 1 and 2 with a corresponding graph illustrating the ultrasonic energy along the length of the trocar.

As is shown in FIG. 7 the amplitude of vibration depends on the location along the tip, with zero amplitude at the nodal points and a maximum amplitude at antinode points, i.e., where the magnitude of the sine of the vibrational waveform is equal to one. The distance of an antinode from its nearest nodal point is ¼ wavelength. The distal end of the tip 24 is at an antinode.

The generator 62 includes a control unit 63 (FIG. 6), an input plug (not shown) which may be plugged into either an electrosurgery unit or a wall outlet, and output wires 60, 61. An input cord 64 is connected from a triggering mechanism 67, to the control unit 63 of the generator. The triggering mechanism 67 communicates with the control unit of the generator to supply ultrasonic energy to the trocar tip. In this embodiment the triggering mechanism 67 is a foot activated switch which may be controlled by the surgeon.

In another embodiment the triggering mechanism is a reset button located on the housing 11 of the trocar assembly. The reset button functions as the foot switch 67 does to switch the trocar assembly 10 from a ready state where the generator is on, the trocar is idling and initial parameters have been measured, to an active state where energy is being delivered to the tip.

The generator 62 sends electrical energy by way of wire 60 to the active electrodes 25 which is returned through ground electrodes 26 and then wire 61. The energy causes the piezoelectric ceramic pieces to vibrate, which cause the obturator to vibrate at a predetermined resonant ultrasonic frequency. The resulting ultrasonic energy is transmitted to the amplifier 22. The amplifier 22, due to its configuration, amplifies the ultrasonic energy which is then transmitted down the waveguide 23 to the tip 24.

The amplitude is dependent on the conservation of momentum due to the change in diameter of the obturator. A tip displacement of from 10 to 300 microns is preferred.

The frequency of the obturator is predetermined. The frequency is preferably high enough so that it is out of the human audible range, i.e. above 20 khz. It is believed that for a constant amplitude, the higher the frequency the more cavitation effect will occur. However, as frequency increases tip amplitude is more difficult to realize because of mass inertia. Thus, a frequency in the range of 20 khz to 150 khz is preferred.

A feedback mechanism is included which measures either continuously or periodically, the load condition of the trocar tip to determine if a preset load condition exists. The control unit acts as a means for controlling the energy supplied to the obturator based on feedback from the feedback mechanism. In this particular embodiment, the control unit automatically shifts its operation between an active state and an inactive state, i.e., idling or completely off, depending on the load condition determined by the feedback mechanism.

Figure 14:
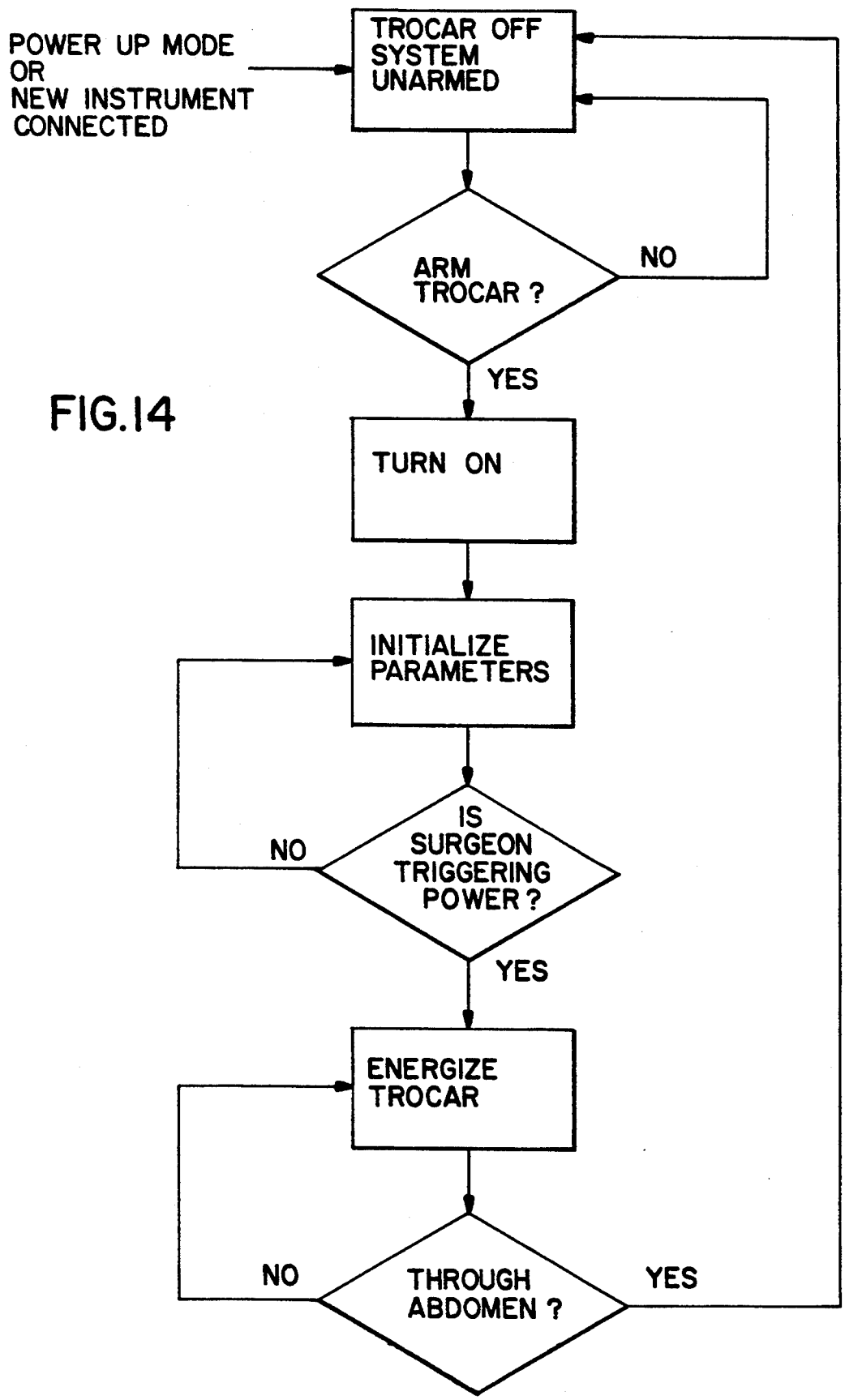
FIG. 14 is a flow chart illustrating use of the trocar of the present invention.
Figure 15:
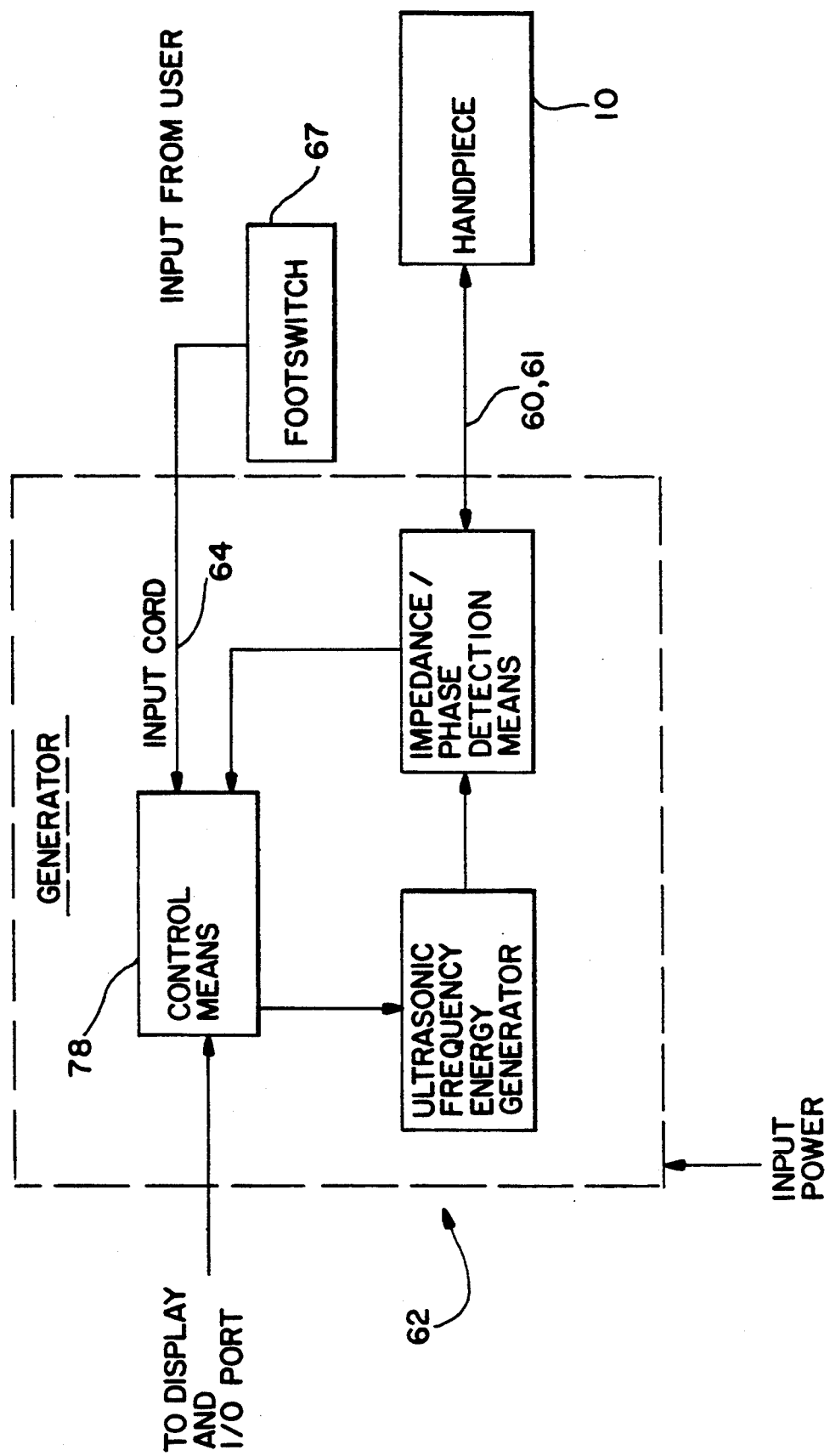
FIG. 15 is a flow chart illustrating the use of the impedance feedback system of the present invention.
Figure 16:
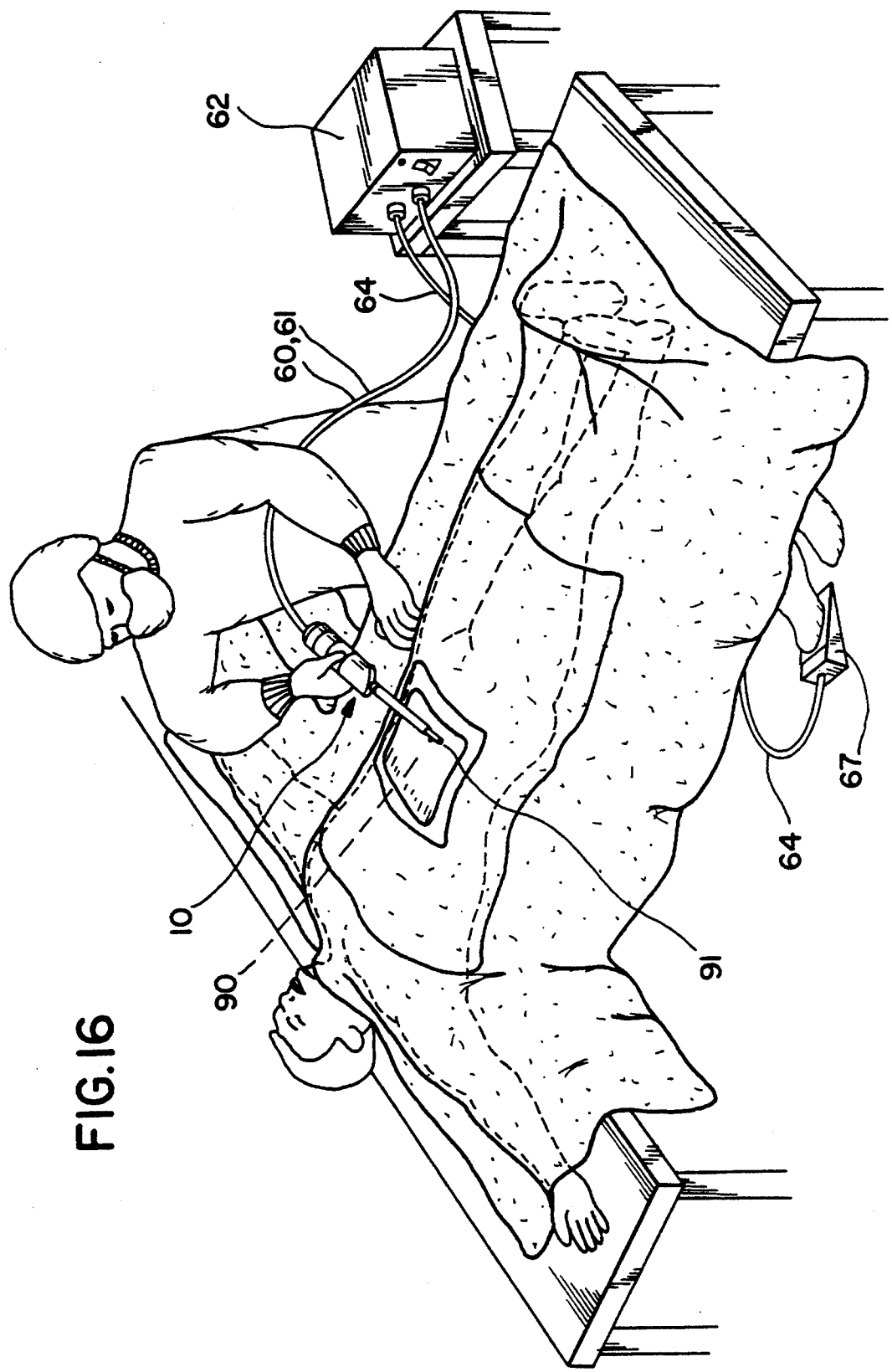
FIG. 16 illustrates the trocar obturator of the present invention in use on a patient to perform abdominal laparoscopic surgery.

FIGS. 14–16 illustrate one use of the trocar assembly of this invention. After a patient's abdominal cavity 90 has been insufflated with carbon dioxide, using, for example, a Verress-type insufflation needle, the trocar tip 24 is located where a puncture 91 is to be made. The trocar assembly is connected to the generator in an unarmed state. The generator then measures the initial parameters of the obturator, i.e. without a tip load, and arms the system, i.e., without a tip load. The trocar is then in a ready state at which point the surgeon may trigger the power using a triggering mechanism 67, e.g., a foot switch or reset button. The surgeon places the trocar assembly at an insertion site. Ultrasonic energy is delivered to the tip while the surgeon applies a minimal force until the trocar is through the insertion site. It is believed that the active or energized tip of the waveguide causes mechanical pressure and tissue cavitation which causes the obturator to penetrate tissue.

When the feedback mechanism detects a no load condition on the trocar tip 24 the control unit turns off the ultrasonic energy. The power may not be turned on again unless the triggering mechanism 67 is used. The trocar 10 may be reset by releasing the triggering mechanism. This mechanism provides a safety feature which, among other things, prevents accidental repowering of the instrument when the trocar has already penetrated tissue and turned itself off.

In a preferred embodiment the load on the tip is measured periodically and a maximum load is determined. When the load decreases in the amount of a predetermined percentage decrease of the maximum load, a preset load condition is indicated. In a preferred embodiment, the preset load condition indicates a no-load condition at which point the trocar tip has penetrated tissue and the trocar is turned off by the shut off mechanism.

Figure 6:
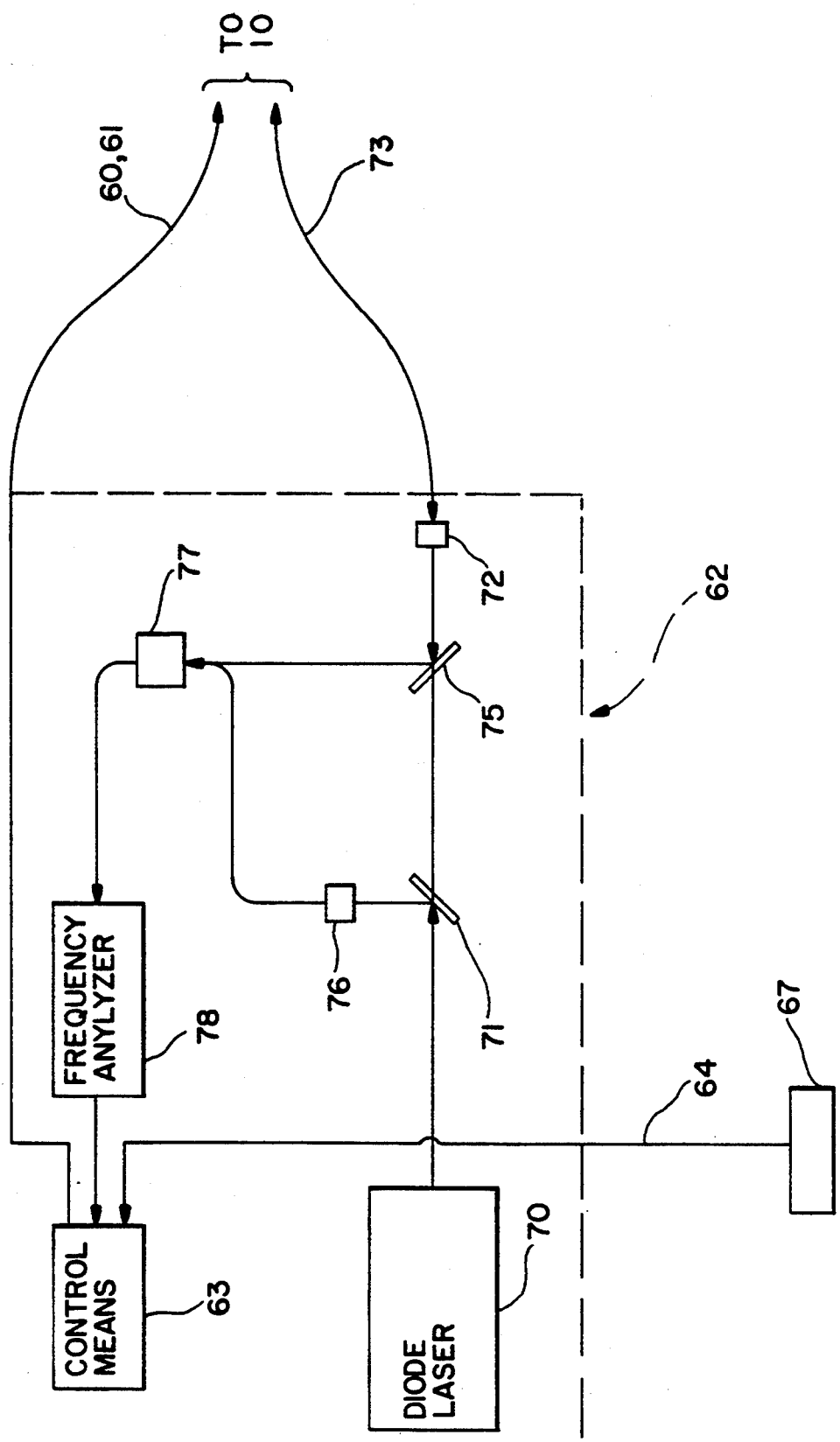
FIG. 6 illustrates a tissue impedance feedback circuit of the trocar assembly illustrated in FIG. 7.

Referring to FIG. 6 one embodiment of a feedback mechanism is illustrated. A light source 70 comprised of a diode laser emits light to a beam splitter 71 where the light is split into a reference beam and a handpiece beam. The diode 70 is coupled to a light fiber 73 at a fiber coupler 72. The light fiber 73 extends through an opening 74 in the proximal end of the housing 11 (FIG. 74). The light fiber 73 directs the handpiece beam towards the proximal end of the end mass 20. The light is reflected off the end mass 20 and is doppler shifted by the vibrating end mass 20. The handpiece beam travels back through the light fiber 73, a beam splitter 75 and then to a photodetector 77. The reference beam which was split at the beam splitter 71, is also received by the photodetector 77 through a fiber coupler 76. The reference beam and handpiece beam are modulated to create a beat frequency which is converted by the photodetector 77 into a modulated electrical signal. The modulated electrical signal is sent to a frequency analyzer 78 which determines the load on the trocar tip based on the doppler shift determined by the beat frequency. The frequency analyzer 78 communicates with the control means 63 of the generator. The control means 63 turns the trocar off at the appropriate load level.

In addition to being adapted for detection of either load/no-load conditions, the feedback mechanism may be specific tip load level, or a change in load.

The user may cause an increase in impedance by applying more pressure when inserting the trocar. As a safety feature, the instrument also may be adapted to be sensitive to the amount of pressure applied by a user to permit the user to release pressure to turn off the ultrasonic energy at any time before, during or after trocar penetration has occurred. The instrument may also be adapted to turn off at a ceiling impedance or load level. This feature will permit the instrument to turn off when an unusually high impedance level is reached, for example, because the tip has reached bone or because the instrument is cracked or fractured in which case the impedance measured at the tip will appear high.

In another embodiment, the feedback mechanism may be used to adjust the ultrasonic energy level in response to change in tissue consistency as reflected in the tip load. The feedback mechanism can detect the load and increase the energy to the transducer to compensate for loss of energy to tissue and resulting decrease in tip displacement due to the load.

The obturator may be semi-reusable or for single patient use and packaged with at least one disposable trocar and may be designed to connect to current disposable trocar cannulas.

Figure 10:
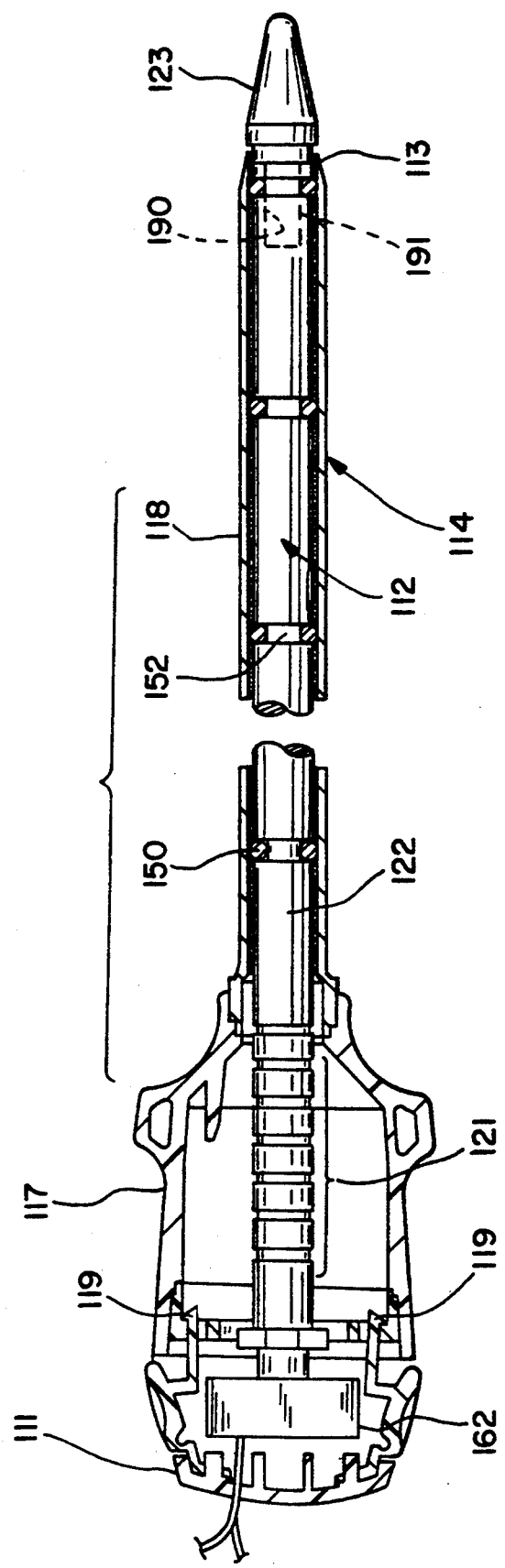
FIG. 10 illustrates a cross-sectional plan view of a trocar assembly of another embodiment of the present invention with a cut away section.
Figure 11:
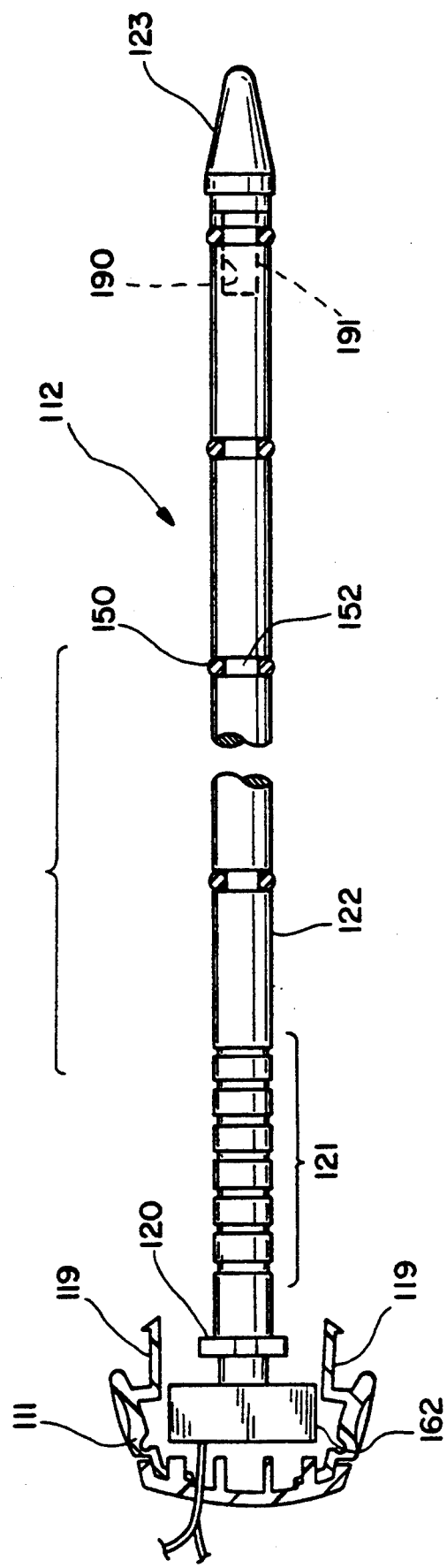
FIG. 11 illustrates a cross-sectional plan view of the trocar obturator of the trocar assembly of FIG. 10.
Figure 12:
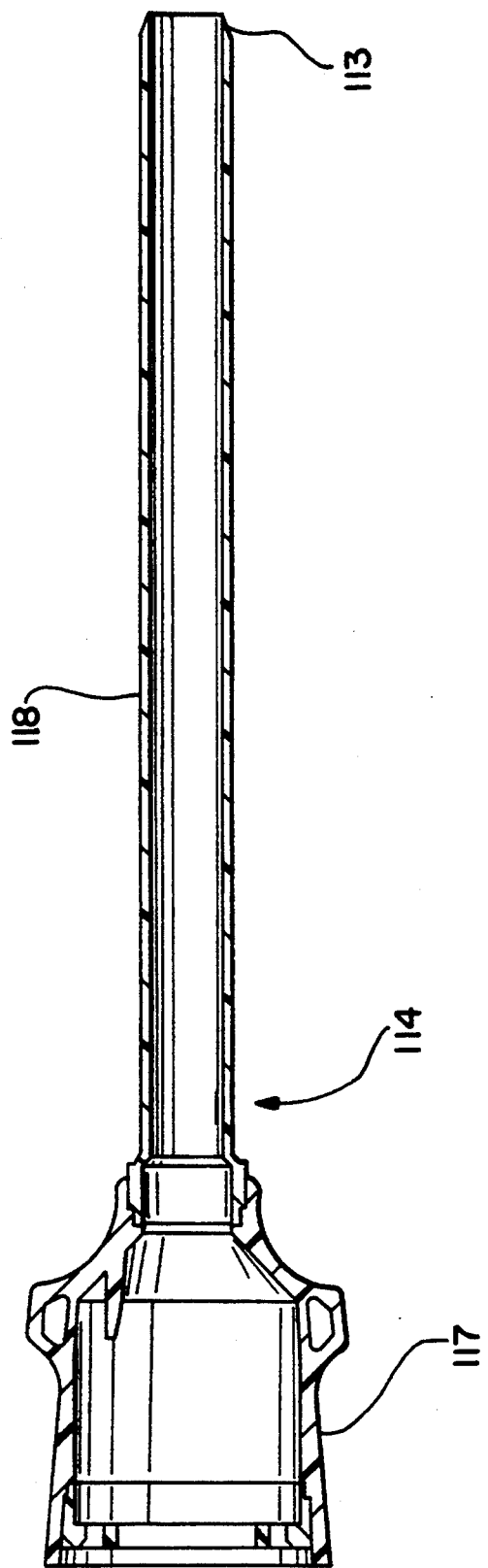
FIG. 12 illustrates a cross-sectional plan view of the trocar assembly of FIG. 10.
Figure 13:
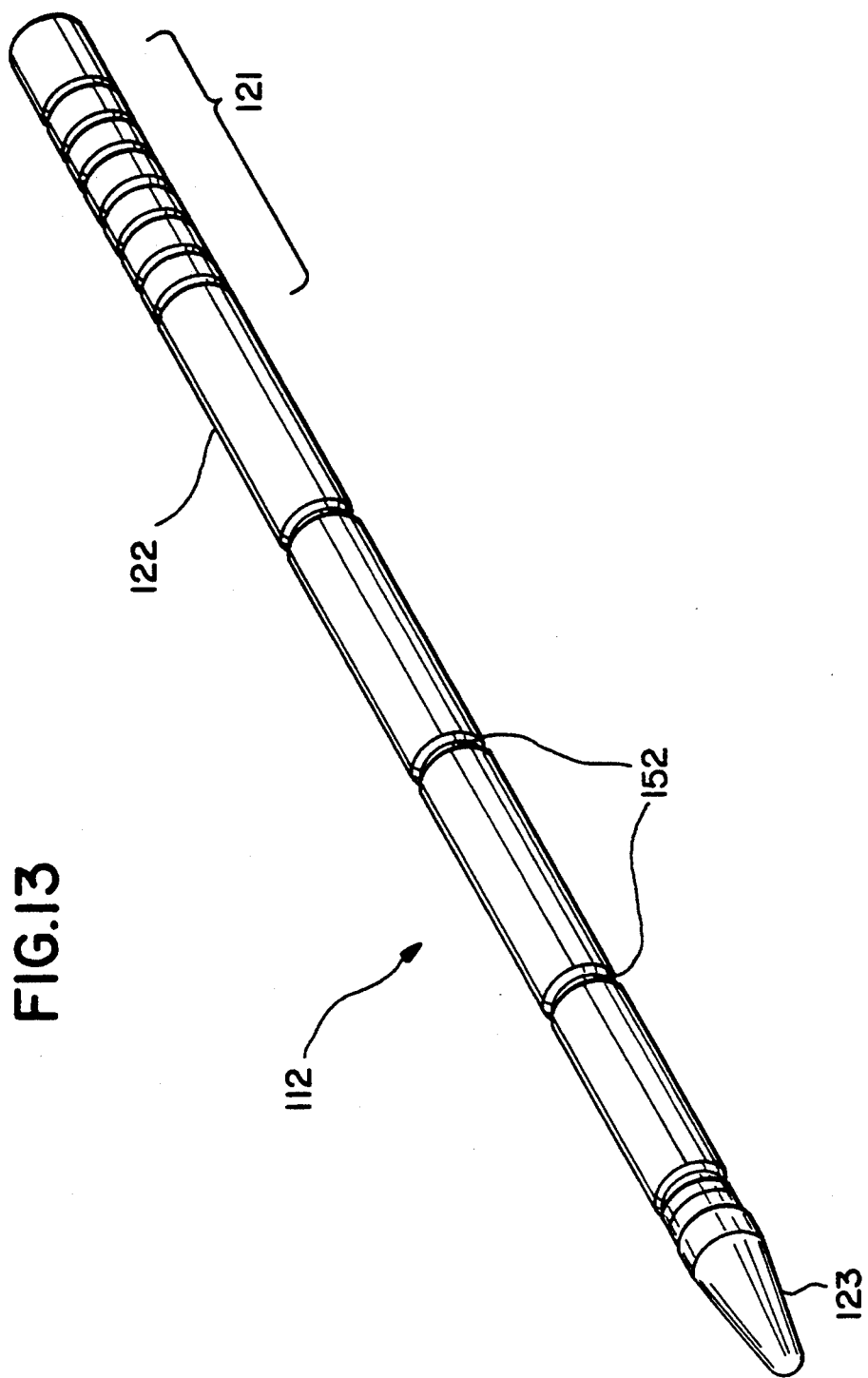
FIG. 13 illustrates perspective view of a trocar shaft of FIG. 11.

Referring now to FIGS. 10-12 there is illustrated another embodiment of the present invention. The trocar assembly 100 comprises an obturator 112 and a cannula 114. The obturator 112 comprises a housing 111 coupled at a proximal end 120 to an obturator shaft 122. The obturator shaft 122 comprises a piezoelectric transducer 121 integral with the obturator shaft 122 for converting electrical energy into ultrasonic energy which is transmitted along the length of the shaft 122 to a tip 123. The tip 123 is coupled to a threaded bore 190 at the distal end of the shaft by a threaded proximal end 191. The shaft has indentations 152 at nodal points to accommodate o-rings 150.

The cannula assembly 114 comprises a handle 117 and a cannula tube 118 attached thereto.

The obturator housing 111 has connector prongs 119 which are received by the cannula handle 117 to couple the cannula 114 to the obturator 112. The obturator 112 is insertable through the cannula handle 117 and cannula tube 118 so that the obturator tip 123 extends from a tapered distal end 113 of the cannula tube 118. The o-rings 150 located at nodal points along the obturator shaft 122 serve to isolate the cannula 114 from the active obturator. The ultrasonic energy is amplified at the obturator tip 123.

In this embodiment high voltage electronic generating elements 162 are embedded in the obturator housing 111 which act as a generator to provide energy to the transducer 121 while drawing energy from an electrosurgery generator, or wall AC-outlet. Energy may optionally be supplied from generator exterior to the housing.

It may be observed from the above that numerous equivalents or modifications may be made without departing from the spirit and scope of the invention. No limitation to the claimed invention is intended from the specific embodiments described herein.

What is claimed is:

1. A trocar assembly comprising
    a cannula comprising a cannula handle and a cannula tube extending from said cannula handle;
    an obturator comprising: an ultrasonic transducer, a solid blunt puncturing tip and a shaft wherein said obturator is adapted to be inserted through said cannula tube; and
    a housing containing said ultrasonic transducer,
    wherein said shaft has a proximal end coupled to said transducer and a distal end coupled to said blunt tip; and
    wherein electrical energy is supplied to the transducer to cause the transducer to vibrate at a selected frequency and propagate vibrations along the shaft to the tip.

2. The trocar assembly of claim 1 wherein said housing is adapted to be used as a handle to manipulate the trocar assembly.

3. The trocar assembly of claim 1 further comprising a connector which secures the transducer to the housing at a nodal point.

4. The trocar assembly of claim 3 wherein the housing connector comprises a distal end with a coupling means for coupling the housing connector to the cannula, said coupling means adapted to be received by the proximal end of the cannula handle.

5. The trocar assembly of claim 1 wherein said housing further comprises a sheath coaxial with the shaft and fitting over the outer circumference of the shaft; and
    wherein said sheath of said housing is adapted to be inserted through said cannula tube.

6. The trocar assembly of claim 5 wherein said sheath comprises a polycarbonate material.

7. The trocar assembly of claim 5 wherein said obturator further comprises
    isolation means for isolating vibrations along the shaft from said sheath, said isolation means located at least one nodal point.

8. The trocar assembly of claim 7 wherein said isolation means comprises at least one o-ring situated in a corresponding groove formed in said shaft at a nodal point.

9. The trocar assembly of claim 7 wherein said isolation means comprises at least one protrusion extending circumferentially inwardly from the inner circumference of the sheath to contact said shaft at a nodal point.

10. A trocar obturator for puncturing tissue to access a location for endoscopic surgery comprising:
    an ultrasonic transducer
    a solid blunt puncturing tip; and
    a shaft having a proximal end coupled to said transducer and a distal end coupled to said blunt tip;
    wherein electrical energy is supplied to the transducer to cause the transducer to vibrate at a selected frequency and propagate vibrations along the shaft to the tip.

11. The trocar obturator of claim 10 wherein the transducer comprises piezoelectric elements.

12. The trocar obturator of claim 10 wherein the transducer comprises magnetorestrictive elements.

13. The trocar obturator of claim 10 further comprising a housing containing said ultrasonic transducer.

14. The trocar obturator of claim 10 further comprising an end mass having a distal end wherein the transducer has a proximal end and a distal end and said proximal end of the transducer is coupled to the distal end of said end mass.

15. The trocar obturator of claim 10 further comprising an amplifier coupled to the proximal end of the shaft and the distal end of the transducer.

16. The trocar obturator of claim 10 further comprising
an energy source for supplying electrical energy to said ultrasonic transducer.

17. The trocar obturator of claim 16 wherein the energy source comprises a generator remote to the trocar housing.

18. The trocar obturator of claim 16 wherein the energy source comprises electronic generating elements contained within the housing.

19. The trocar obturator of claim 10 wherein the ultrasonic transducer is integral with said shaft of said obturator.

20. The trocar obturator of claim 10 further comprising a feedback mechanism for determining variations in load on the trocar tip and a control means for controlling the energy supplied to the obturator based on feedback from said feedback mechanism.

21. The trocar obturator of claim 20 wherein said control means further comprises a shut off mechanism for turning off the deliverance of ultrasonic energy to the obturator tip when the feedback mechanism determines the existence of a preset load condition.

22. The trocar obturator of claim 21 wherein the preset load condition indicates that the trocar has penetrated tissue.

23. The trocar obturator of claim 21 wherein the preset load condition indicates one or more tissue characteristics of tissue loading the trocar tip.

24. The trocar obturator of claim 21 further comprising a reset mechanism which must be used every time the trocar is turned off by the shut off mechanism before it can be powered up again.

25. The trocar obturator of claim 20 wherein said feedback mechanism comprises a light source and a light receptor located on the housing, wherein said light source directs light towards an active portion of the obturator, wherein said light receptor receives light reflected from the active portion, wherein said light reflected has a doppler shifted frequency related to the load on the tip from which load on the trocar tip is determined.

26. The trocar obturator of claim 20 wherein the feedback mechanism uses electrical parameters voltage and current supplied to the transducer to determine variations in load on the trocar tip.

27. The trocar obturator of claim 26 wherein the electrical parameters used to determine load on the trocar tip are phase shift differences between voltage and current.

28. The trocar obturator of claim 26 wherein the electrical parameters used to determine load on the trocar tip are ratios of the voltage and current magnitudes supplied to the transducer.

29. The trocar obturator of claim 20 wherein the control means is capable of adjusting the amount of energy supplied to the obturator to compensate for changes in load to provide a relatively stable energy level at the obturator tip.

30. The trocar obturator of claim 20 wherein said preset load level is a ceiling impedance level.

31. The trocar obturator of claim 16 further comprising a triggering mechanism which switches on electrical energy to supply electrical energy to the obturator.

32. The trocar obturator of claim 31 wherein said triggering mechanism comprises a foot activated switch coupled to said energy source.

33. The trocar obturator of claim 31 wherein said triggering mechanism comprises a reset button associated with said obturator, said reset button, when depressed, switching on the energy supplied to the obturator.

* * * * *